United States Patent [19]

Tomita et al.

[11] Patent Number: 5,317,084
[45] Date of Patent: May 31, 1994

[54] PROCESS FOR LARGE-SCALE PRODUCTION OF ANTIMICROBAL PEPTIDE IN HIGH PURITY

[75] Inventors: Mamoru Tomita; Seiichi Shimamura, both of Kanagawa; Kozo Kawase, Saitama; Yasuo Fukuwatari, Kanagawa; Mitsunori Takase, Saitama; Wayne Bellamy, Kanagawa; Tomoyuki Hagiwara, Kanagawa; Hiroyuki Matukuma, Kanagawa, all of Japan

[73] Assignee: Morinaga Milk Industry Co., Ltd., Tokyo, Japan

[21] Appl. No.: 891,174

[22] Filed: May 29, 1992

[30] Foreign Application Priority Data

Jun. 21, 1991 [JP] Japan .................. 3-150604

[51] Int. Cl.$^5$ .......... C12N 9/08; C07K 3/22; C07K 13/00
[52] U.S. Cl. ................ 530/324; 530/344; 435/68.1
[58] Field of Search .......... 530/395, 397, 803, 833, 530/344, 324; 435/68.1

[56] References Cited

U.S. PATENT DOCUMENTS 5,149,647  9/1992  Burling ................ 530/366

*Primary Examiner*—Howard E. Schain
*Assistant Examiner*—P. Lynn Touzeau
*Attorney, Agent, or Firm*—Wenderoth, Lind & Ponack

[57] ABSTRACT

Lactoferricin (Trade Mark), also called LFCIN (Trade Mark), a potent antimicrobial peptide, is produced by contacting an enzymatic hydrolysate of bovine lactoferrin or any mixture of peptides containing lactoferricin preferably with a butyl moiety-containing hydrophobic interaction chromatography medium, or alternatively with a carboxymethyl moiety-containing cation-exchange chromatography medium, rinsing the medium to remove unbound peptides, desorbing the lactoferricin solution at constant pH, and desalting the desorbed solution. The utility of the process is illustrated, for example, as follows. An enzymatic hydrolysate of bovine lactoferrin (600 g) was contacted with 3000 ml of BUTYL-TOYOPEARL 650M, the medium was rinsed with water, and then with McIlvaine (citric acid-sodium phosphate) buffer at pH 7.0., and lactoferricin was desorbed with McIlvaine buffer at pH 5.0. The desorbed material was desalted by contacting it with BUTYL-TOYOPEARL 650M, rinsing the medium with water to remove the buffer salts, and desorbing the lactoferricin with 10 mM HCl. A yield of 10.5 g of 99% purity was obtained. The product has applications as a safe and effective antimicrobial agent for use in oral hygiene products, cosmetics, clinical foods, etc.

12 Claims, 1 Drawing Sheet

FIG. 1

PROCESS FOR LARGE-SCALE PRODUCTION OF ANTIMICROBAL PEPTIDE IN HIGH PURITY

FIELD OF THE INVENTION

This invention relates to a process for large-scale production of a potent antimicrobial peptide [hereinafter referred to as lactoferricin (Trade Mark)] in high purity.

More particularly, this invention relates to a process for producing the lactoferricin useful for preparing a safe and effective antimicrobial agent, of at least 90% purity in substantial quantities, that is, at least gram quantities.

PRIOR ART

Lactoferrin is a non-heme iron-binding glycoprotein present in various biological fluids of mammals including milk, saliva, tears, semen and raucous secretions. It is a multifunctional protein having iron absorptive, cell growth-promoting, immune-modulating, and antimicrobial activities. Large quantities of bovine lactoferrin can be obtained by extracting this protein from raw skim milk or cheese whey originating from the milk of cows and, consequently, bovine lactoferrin is readily available as a commercial product of the dairy industry.

Lactoferricin, also called LFCIN (Trade Mark), is a potent antimicrobial peptide of commercial value derived from bovine lactoferrin by enzymatic cleavage and, for example, consisting of a single peptide chain of 25 amino acid residues having the sequence Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe, as disclosed in U.S. patent application Ser. No. 07/755,161. Lactoferricin has potent, broad spectrum antimicrobial properties. It is effective at low concentrations against various species of Gram-positive and Gram-negative bacteria, and yeasts, including strains known to cause disease in humans and animals. The effect of lactoferricin is microbicidal, that is, lethal to microorganisms, causing a rapid loss of microbial colony-forming ability. Most other antimicrobial agents, including all clinically used antibiotics, are structurally complex chemicals that are foreign to the bodies of humans and animals. On the other hand, lactoferricin is considered to be a healthy and safe product because it is a natural peptide containing no unusual amino acids or foreign chemical groups. It is probably produced naturally in the stomach of humans by gastric pepsin digestion of bovine lactoferrin found in cow's milk, a commonly consumed food. Accordingly, lactoferricin has commercial value as a safe and effective antimicrobial agent for use in numerous applications including, for example, eye-care products, oral hygiene products, cosmetics and skin care products, clinical foods, pet hygiene products, etc.

For many such applications it is considered preferable to use lactoferricin of at least 90% purity rather than a crude preparation. Lactoferricin of high purity is considered less likely to cause undesirable changes in the functional properties of a given product such as taste, odor, color, texture, immunogenicity, etc., as compared to a crude preparation, because a smaller quantity of purified lactoferricin is required to achieve a desired antimicrobial effect. Moreover, it is possible that undesirable changes in the functional properties of a given product might be imparted by components other than lactoferricin contained in a crude preparation of lactoferricin.

A process for large-scale production of lactoferricin in high purity is essential to provide substantial quantities of this product for commercial use. Very small quantities of lactoferricin, that is, up to about one milligram, may be obtained in high purity on an analytical-scale by a process of reverse-phase high performance liquid chromatography as disclosed in U.S. patent application Ser. No. 07/755,161. This analytical-scale method is suitable for assaying the purity of lactoferricin but it is unable to provide substantial quantities of this product for commercial use. For large-scale production of lactoferricin, a suitable process is one which is able to provide lactoferricin of at least 90% purity in substantial quantities, that is, at least gram quantities. No process for producing such quantities of lactoferricin in high purity has been described previously.

With the intention of creating a process to provide lactoferricin for commercial use, the present inventors have studied the interaction of lactoferricin with various chromatographic media under various conditions and have investigated new methods for purification of this antimicrobial peptide. As a result, they have created a new process for producing substantial quantities of lactoferricin in high purity and thereby have completed this invention.

SUMMARY OF THE INVENTION

The object of the present invention lies in providing a process for producing substantial quantities of lactoferricin in high purity.

That is, our invention contemplates to provide a process consisting of contacting a mixture of peptides containing lactoferricin which is prepared by enzymatically hydrolyzing bovine lactoferrin or bovine milk protein containing lactoferrin with a hydrophobic chromatographic medium or cation-exchange chromatographic medium to adsorb the lactoferricin, rinsing the medium to elute peptides other than the lactoferricin, desorbing the lactoferricin in solution from the rinsed medium, and desalting the desorbed lactoferricin solution, whereby the lactoferricin of at least 90% by weight purity is obtained.

DETAILED DESCRIPTION OF THE INVENTION

The starting material used in the present invention is any mixture of peptides containing lactoferricin.

Preferably, the starting material is prepared by enzymatic digestion of pure bovine lactoferrin. Alternatively, it is possible to prepare the starting material by enzymatic digestion of a crude preparation of bovine lactoferrin, or any mixture of milk proteins which includes bovine lactoferrin as a component. The enzyme used for this digestion is preferably pepsin, however, any protease which is capable of cleaving bovine lactoferrin to generate lactoferricin may be used.

The starting material is dissolved preferably in pure water. Alternatively, a buffer solution or salt solution may be used. The pH of the starting material is adjusted to 6.5 to 7.5, preferably 7.0.

Any insoluble substances in the starting material, if present, are removed by conventional methods such as by centrifugation or filtration.

A suitable method for preparing the starting material is exemplified as follows. Bovine lactoferrin isolated from skim milk or cheese whey is dissolved in distilled water at a concentration of 5% (w/v) and the pH is adjusted to 3.0 by addition of 1N HCl. Pepsin is added to a final concentration of 3% (w/w of substrate) and hydrolysis is performed at 37° C. for 4 h. The reaction may be terminated by heating at 80° C. for 15 min, if desired, although termination of the reaction is unnecessary. The pH of the resulting peptide mixture is adjusted to 7.0 by addition of 1N NaOH. Any insoluble peptides are removed from the starting material by centrifugation at 15000 x g for 30 min.

If desired, the starting material may be dried by conventional means, for example, by freeze-drying or spray-drying, and stored as a dry powder until used. The dry powder is rehydrated by dissolving preferably in pure water before use. Alternatively, the starting material in aqueous solution may be used directly, that is, without drying and rehydrating, for production of lactoferricin.

Lactoferricin may be produced by any of the following methods.

In one method, most preferably, lactoferricin is produced by contacting the starting material, that is, a mixture of peptides containing lactoferricin, with a butyl moiety-containing hydrophobic interaction chromatography medium, rinsing the medium to remove unbound peptides, desorbing the lactoferricin at a constant pH, preferably pH 4.8-5.2, and desalting the lactoferricin product. Any butyl-containing hydrophobic interaction chromatography medium may be used. A suitable medium, for example, is BUTYL-TOYOPEARL (Tosoh Corp.) or BUTYL-SEPHAROSE (Pharmacia), but BUTYL-TOYOPEARL is preferred. Furthermore, the present inventors have demonstrated for the first time that lactoferricin has affinity for hydrophobic materials and surfaces, as indicated by its affinity for a medium having a butyl moiety and, consequently, it is obvious to those skilled in the art that other hydrophobic media such as those containing a hexyl, octyl, phenyl, or octylamine moiety should be similarly effective for use in this method. The hydrophobic medium is rinsed and equilibrated with water before use. The process may be performed using a stirred tank or a chromatography column or a combination of both. Preferably, the starting material is initially contacted with the medium in a stirred tank, then the liquid is collected, the medium is transferred to a chromatographic column, and the collected liquid is again contacted with the medium in the column. After contacting the starting material with the hydrophobic medium, the medium is rinsed with water to remove the unbound peptides which may be recovered as a useful by-product of the process having nutritional value. Rinsing of the medium is continued until the protein content of the water eluted from the medium declines to a low level, as indicated by an absorbance at 280 nm of about 0.06 or less. After rinsing the medium with water, a buffer is introduced into the system. It is prossible to introduce the buffer by rinsing the hydrophobic medium directly with the buffer. Alternatively, and preferably, the buffer is introduced by desorbing the bound peptides including lactoferricin from the medium with a dilute solution of acid, mixing the buffer with the desorbed peptides, recontacting the resulting buffered peptide solution with the hydrophobic medium, and rinsing the medium with the same buffer. A suitable acid, for example, is one selected from the group consisting of HCl, $H_2SO_4$, $H_3PO_4$, acetic acid and citric acid, but HCl is prefered. The final concentration of the acid is 1-30 mM, preferably 10 mM. A suitable buffer, for example, is one selected from the group consisting of $NaH_2PO_4$-$Na_2HPO_4$, $KH_2PO_4$-$K_2HPO_4$, $NaH_2PO_4$-$K_2HPO_4$, $KH_2PO_4$-$Na_2HPO_4$, citric acid-$Na_2HPO_4$, acetic acid-sodium acetate, but citric acid-$Na_2HPO_4$ is preferred. The final concentration of the buffer is 20 to 200 mM, preferably 100-200 mM, and the final pH of the buffer is 6.5-7.5, preferably pH 7.0. Lactoferricin is desorbed selectively from the medium at a constant pH using the same buffer adjusted to a final pH of 4.5-5.5, preferably 4.8-5.2. Desalting of the lactoferricin solution thus obtained is performed as described below. Other material which remains bound to the hydrophobic medium may be recovered as a by-product of the process by desorbing the material with a dilute solution of acid, preferably 10-20 mM HCl and, since this by-product contains some lactoferricin, it may be used in applications which do not require lactoferricin of high purity. The hydrophobic medium is rinsed with water and, thus treated, may be reused.

In an alternative method, lactoferricin is produced by contacting the starting material with a carboxymethyl moiety-containing cation-exchange chromatography medium, rinsing the medium to remove the unbound peptides, desorbing the lactoferricin with a salt solution at pH 7-8, and desalting the product. Any cation-exchange medium which contains a carboxymethyl moiety may be used. A suitable medium, for example, is one selected from the group consisting of CARBOXYMETHYL-TOYOPEARL (Tosoh Corp.), CARBOXYMETHYL-SEPHADEX (Pharmacia), CARBOXYMETHYL-BIO-GEL A AGAROSE (BioRad Laboratories), and CARBOXYMETHYL-CELLULOSE (BioRad Laboratories), but CARBOXYMETHYL-TOYOPEARL is prefered. The cation-exchange medium is rinsed and equilibrated with a buffer before used. A suitable buffer, for example, is one selected from the group consisting of $NaH_2PO_4$-$Na_2HPO_4$, $KH_2PO_4$-$K_2HPO_4$, $NaH_2PO_4$-$K_2HPO_4$, $KH_2PO_4$-$Na_2HPO_4$, citric acid-$Na_2HPO_4$, acetic acid-sodium acetate and Glycine-NaOH, but $NaH_2PO_4$-$Na_2HPO_4$ or $KH_2PO_4$-$K_2HPO_4$ is preferred. The final concentration of the buffer is 10-200 mM. The process may be performed using a stirred tank or a chromatography column or a combination of both. Preferably, the starting material is initially contacted with the medium in a stirred tank, then the liquid is collected, the medium is transfered to a chromatographic column, and the collected liquid is again contacted with the medium in the column. After contacting the starting material with the cation-exchange medium, the medium is rinsed with the buffer to remove the unbound peptides which may be recovered as a useful by-product of the process having nutritional value. Rinsing of the medium is continued until the protein content of the buffer eluted from the medium declines to a low level, as indication by an absorbance at 280 nm of about 0.06 or less. The lactoferricin is desorbed from the cation-exchange medium with a salt solution. A suitable salt is one selected from the group consisting of ammonium acetate, ammonium chloride, KCl, and NaCl, but ammonium acetate or ammonium chloride is prefered. The final concentration of the salt is 1–4M, preferably 2M or more. In the case of ammonium chloride or ammonium acetate the salt solution is prepared in water, however, in the case of NaCl or KCl the salt solution is prepared in the buffer indicated above. The final pH of the salt solution is adjusted to 7–8. Desalting of the lactoferricin solution thus obtained is performed as described below. The cation-exchange medium is rinsed with the buffer and, thus treated, may be reused.

Desalting of the lactoferricin solution obtained by any of the foregoing methods may be accomplished as follows.

Preferably, desalting of the lactoferricin solution is accomplished using the hydrophobic interaction chromatography medium. The lactoferricin solution is adjusted to pH 7–8 and then contacted with the hydrophobic medium. The medium is rinsed with water to remove the buffer salts and lactoferricin is desorbed with a dilute solution of acid, preferably 10 mM HCl, to obtain the final product. The hydrophobic medium is reconditioned by rinsing with water and thus treated may be reused.

Alternatively, desalting of the lactoferricin solution may be accomplished by conventional means, such as by electrodialysis or ultrafiltration, for example, using a semipermeable membrane or hollow fiber filter cartridge having a molecular weight cut-off of 3000 or less which retains the lactoferricin but allows the salts to pass through, thereby facilitating the removal of salts.

If desired, the desalted lactoferricin thus obtained may be dried by conventional means, for example, by freeze-drying or spray-drying, to give a white powder.

The lactoferricin produced according to the process of the present invention has a purity of at least 90%.

The lactoferricin produced according to the process of the present invention is functionally active having potent broad spectrum antimicrobial activity.

According to the process of the present invention, any desired quantity of lactoferricin of high purity can be produced. The quantity of lactoferricin obtained is dependent only on the amount of lactoferricin in the starting material and the amount of chromatographic medium used. Using the methods of the present invention, up to about 0.3–0.5 grams of lactoferricin can be produced using 100 ml of chromatographic medium, and up to about 3–5 grams of lactoferricin can be produced using 1000 ml of chromatographic medium. That is, the yield of lactoferricin can be increased about 10-fold by increasing the amount of chromatographic medium by 10-fold and appropriately increasing the amount of starting material used. Obviously, through further scale-up to the process, the present invention provides the means to produce lactoferricin of high purity in any desired quantity, for example, several hundred grams, or several hundred kilograms, or more.

The above disclosure generally describes the present invention. A more complete understanding can be obtained by reference to the following Tests for the various aspects of the invention.

Test 1

Figure 1:
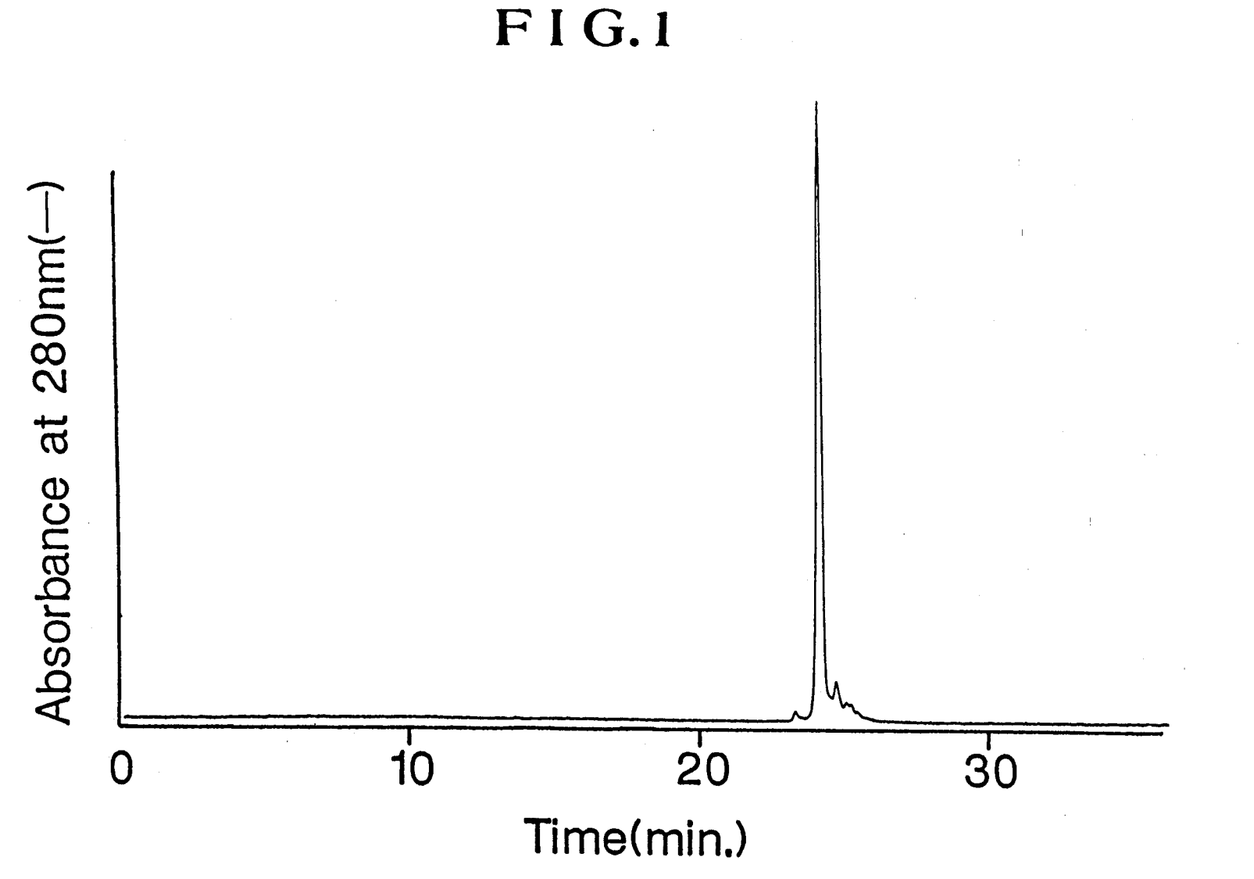
FIG. 1 exhibits an example of reverse-phase high performance chromatography profile of a sample of lactoferricin having a purity of 90%.

The purity of the lactoferricin obtained may be determined by reverse phase high performance liquid chromatography as follows. The test sample containing lactoferricin is fractionated on a column of TSK-GEL 120T (0.6×150 mm; Tosoh Corp.) eluted with a mixture 80:20 of eluents A (0.005% trifluoroacetic acid) and B (90% acetonitrile in 0.05% trifluoroacetic acid) for 10 min followed by a linear gradient of A:B from 80:20 to 40:60 for 30 min at a flow rate of 0.8 ml/min. The absorbance at 280 nm of the eluted peptides is recorded on a printer-plotter and the relative concentrations of peptide components in the sample applied are determined from the relative sizes of the peptide peaks. For example, the reverse-phase high performance chromatography profile of a sample of lactoferricin having a purity of 90% prepared as described below in Example 2 is shown in FIG. 1.

Test 2

The effects of various buffers and pH conditions on elution of lactoferricin from the butyl moiety-containing hydrophobic interaction chromatography medium are exemplified as follows.

For use as the starting material, 2.0 g of the peptide mixture obtained in Example 1 was dissolved in water at a final concentration of 5% (w/v). BUTYL-TOYOPEARL 650M was rinsed and equilibrated with water before use. In a series of experiments, 100 mg of the starting material in aqueous solution was contacted with 5.0 ml of the hydrophobic medium, the medium was rinsed with water to remove unbound peptides, then rinsed with buffer (Rinse Buffer, TABLE 1). The bound lactoferricin was eluted with buffer (Elution Buffer, TABLE 1). Among these buffers, McIlvaine buffer was prepared by combining appropriate volumes of 0.1M citric acid and 0.2M $Na_2HPO_4$ to obtain the final pH indicated in TABLE 1. The concentration of all other buffers used was 100 mM. The yield (mg) of lactoferricin obtained using various buffers and pH conditions was determined from the equation $[Y = A/2.203 \times V]$, where Y is the yield of lactoferricin, A is the absorbance at 280 nm of the eluted lactoferricin solution, V is the total volume of the eluted lactoferricin solution, and 2.203 is the absorbance of a standard solution (1.00 mg/ml) of purified lactoferricin. The purity (%) of the lactoferricin was also determined by reverse-phase high performance liquid chromatography as described in Test 1.

These results are summarized in TABLE 1. The results indicate that the highest yield and purity of lactoferricin are obtained by adjusting the pH of the elution buffer to 4.8 to 5.2, preferably 5.0. The results further indicate that McIlvaine buffer, $NaH_2PO_4$-$NaH_2PO_4$, $KH_2PO_4$-$KH_2PO_4$, pH 7.0, or acetic-sodium acetate buffer may be used.

TABLE 1

| Rinse Buffer | Elution Buffer | Lactoferricin Yield (mg) | Purity (%) |
|---|---|---|---|
| McIlvaine, pH 7.0 | McIlvaine, pH 7.0 | 0 | — |
| McIlvaine, pH 7.0 | McIlvaine, pH 6.6 | 0 | — |
| McIlvaine, pH 7.0 | McIlvaine, pH 6.2 | 0.3 | ND |
| McIlvaine, pH 7.0 | McIlvaine, pH 5.8 | 0.4 | ND |
| McIlvaine, pH 7.0 | McIlvaine, pH 5.6 | 0.5 | 99 |
| McIlvaine, pH 7.0 | McIlvaine, pH 5.4 | 1.1 | 98 |
| McIlvaine, pH 7.0 | McIlvaine, pH 5.2 | 1.8 | 98 |
| McIlvaine, pH 7.0 | McIlvaine, pH 5.0 | 2.0 | 98 |
| McIlvaine, pH 7.0 | McIlvaine, pH 4.8 | 2.0 | 97 |
| McIlvaine, pH 7.0 | McIlvaine, pH 4.6 | 2.2 | 93 |
| $NaH_2PO_4$-$Na_2HPO_4$, pH7.0 | $NaH_2PO_4$-$Na_2HPO_4$, pH5.0 | 1.9 | 98 |
| $KH_2PO_4$-$K_2HPO_4$, pH7.0 | $KH_2PO_4$-$K_2HPO_4$,pH5.0 | 1.9 | 98 |

TABLE 1-continued

| Rinse Buffer | Elution Buffer | Lactoferricin Yield (mg) | Purity (%) |
|---|---|---|---|
| HAc-NaAc,pH7.0 | HAc-NaAc,pH5.0 | 1.8 | 97 |

ND: not determined
HAc: acetid acid
sodium acetatl

Test 3

The effects of various acids on elution of lactoferricin from the hydrophobic interaction chromatography medium used for desalting are exemplified as follows.

BUTYL-TOYOPEARL 650M was rinsed and equilibrated with McIlvaine buffer, pH 7.0 (prepared by combining solutions of 0.1M citric acid and 0.2M $Na_2HPO_4$ in a ratio of 177:824) before use. In a series of experiments, 4 mg of purified lactoferricin in McIlvaine buffer, pH 7.0 was contacted with 5.0 ml of the hydrophobic medium, the medium was rinsed with water, then the bound lactoferricin was eluted with 15 ml of acid solution as indicated. The recovery (%) of lactoferricin obtained using various acid solutions was determined from the equation $[R=(A/2.203 \times V)/4 \times 100]$, where R is the recovery of lactoferricin, A is the absorbance at 280 nm of the eluted lactoferricin solution, V is the total volume of the eluted lactoferricin solution, and 2.203 is the absorbance of a standared solution (1.00 mg/ml) of purified lactoferricin and 4 is the amount of purified lactoferricin (mg) initially contacted with the hydrophobic medium.

These results are summarized in TABLE 2. The results indicate that the lactoferricin is eluted at acid concentrations of 1-30 mM but the recovery is highest at concentrations of 10 mM or more. In order to minimize the amount of acid contained in the final product the lowest effective concentration of acid is prefered. That is, the preferred concentration of acid for elution is 10 mM. The results further indicate that HCl, $H_2SO_4$, $H_3PO_4$, acetic acid and citric acid may be used for elution of lactoferricin.

TABLE 2

| Acid Solution | Recovery (%) |
|---|---|
| 1 mM HCl | 3 |
| 2 mM HCl | 12 |
| 5 mM HCl | 26 |
| 10 mM HCl | 98 |
| 20 mM HCl | 99 |
| 30 mM HCl | 99 |
| 10 mM $H_2SO_4$ | 97 |
| 10 mM $H_3PO_4$ | 97 |
| 10 mM acetic acid | 97 |
| 10 mM citric acid | 84 |

Test 4

The effects of various salts on elution of lactoferricin from the carboxymethyl-moiety containing chromatography medium are exemplified as follows.

CARBOXYMETHYL-TOYOPEARL 650S was rinsed and equilibrated with 10 mM $KH_2PO_4$-$K_2HPO_4$ buffer, pH 7.8 before use. In a series of experiments, 4 mg of purified lactoferricin in the same buffer, was contacted with 5.0 ml of the cation-exchange medium, the medium was rinsed with the buffer, then the bound lactoferricin was eluted with 15 ml of salt solution as indicated in TABLE 3. In these solutions, $NH_4$-Acetate and $NH_4CL$ were dissolved in water, NaCl and KCl were dissolved in 10 mM $KH_2PO_4$-$K_2HPO_4$ buffer, and all solutions were adjusted to pH 7.8. The recovery (%) of lactoferricin obtained using various salt solutions was determined in the same manner as in Test 3.

These results are summarized in TABLE 3. The results indicate that the lactoferricin is eluted at salts concentrations of 1-4M but the recovery is highest at concentrations of 2M or more. The results further indicate that NaCl, KCl, $NH_4$- Acetate and $NH_4Cl$ may be used for elution of lactoferricin.

TABLE 3

| Salt Solution | Recovery (%) |
|---|---|
| 0.5 M $NH_4$-Acetate | 2 |
| 1 M $NH_4$-Acetate | 48 |
| 2 M $NH_4$-Acetate | 94 |
| 3 M $NH_4$-Acetate | 95 |
| 2 M $NH_4Cl$ | 94 |
| 1 M NaCl | 4 |
| 2 M NaCl | 12 |
| 3 M NaCl | 64 |
| 4 M NaCl | 72 |
| 3 M KCl | 66 |

---

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
( A ) LENGTH: 20 amino acids
( B ) TYPE: amino acid
( C ) STRANDEDNESS: single
( D ) TOPOLOGY: linear ( i i ) MOLECULE TYPE:

( i i i ) HYPOTHETICAL:

( i v ) ANTI-SENSE:

( v ) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified site
    (B) LOCATION: 2
    (C) IDENTIFICATION METHOD:
    (D) OTHER INFORMATION: /note="thiol group of
        Cys residue at location 2 connected by disulfide bond
        with thiol group of Cys residue at location 19"

(ix) FEATURE:
    (A) NAME/KEY: modified site
    (B) LOCATION: 19
    (C) IDENTIFICATION METHOD:
    (D) OTHER INFORMATION: /note="thiol group of
        Cys residue at location 19 connected by disulfide bond
        with thiol group of Cys residue at location 2"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:1:

Lys Cys Arg Arg Trp Gln Trp Arg Met Lys Lys Leu Gly Ala Pro
1               5                   10                  15

Ser Ile Thr Cys Val
              20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear     (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:

(G) CELL TYPE:
                    (H) CELL LINE:
                    (I) ORGANELLE:

(vii) IMMEDIATE SOURCE:
                    (A) LIBRARY:
                    (B) CLONE:

(viii) POSITION IN GENOME:
                    (A) CHROMOSOME/SEGMENT:
                    (B) MAP POSITION:
                    (C) UNITS:

(ix) FEATURE:
                    (A) NAME/KEY: modified site
                    (B) LOCATION: 2
                    (C) IDENTIFICATION METHOD:
                    (D) OTHER INFORMATION: /note="Cys residue
                        having thiol group chemically modified to prevent
                        disulfide bond formation"

(ix) FEATURE:
                    (A) NAME/KEY: modified site
                    (B) LOCATION: 19
                    (C) IDENTIFICATION METHOD:
                    (D) OTHER INFORMATION: /note="Cys residue
                        having thiol group chemically modified to prevent
                        disulfide bond formation"

(x) PUBLICATION INFORMATION:
                    (A) AUTHORS:
                    (B) TITLE:
                    (C) JOURNAL:
                    (D) VOLUME:
                    (E) ISSUE:
                    (F) PAGES:
                    (G) DATE:
                    (H) DOCUMENT NUMBER:
                    (I) FILING DATE:
                    (J) PUBLICATION DATE:
                    (K) RELEVANT RESIDUES IN SEQ ID NO:

(xi) SEQUENCE DESCRIPTION: SEQ ID NO:2:

Lys  Xaa  Arg  Arg  Trp  Gln  Trp  Arg  Met  Lys  Lys  Leu  Gly  Ala  Pro
 1              5                        10                        15

Ser  Ile  Thr  Xaa  Val
                20

(2) INFORMATION FOR SEQ ID NO:3:

(i) SEQUENCE CHARACTERISTICS:
                    (A) LENGTH: 20 amino acids
                    (B) TYPE: amino acid
                    (C) STRANDEDNESS: single
                    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                    (A) ORGANISM:
                    (B) STRAIN:
                    (C) INDIVIDUAL ISOLATE:
                    (D) DEVELOPMENTAL STAGE:
                    (E) HAPLOTYPE:
                    (F) TISSUE TYPE:
                    (G) CELL TYPE:
                    (H) CELL LINE:
                    (I) ORGANELLE:

(vii) IMMEDIATE SOURCE:
                    (A) LIBRARY:
                    (B) CLONE:

-continued ( v i i i ) POSITION IN GENOME:
                        ( A ) CHROMOSOME/SEGMENT:
                        ( B ) MAP POSITION:
                        ( C ) UNITS:

( i x ) FEATURE:
                        ( A ) NAME/KEY: modified site
                        ( B ) LOCATION: 2
                        ( C ) IDENTIFICATION METHOD:
                        ( D ) OTHER INFORMATION: /note="thiol group of
                                Cys residue at location 2 connected by disulfide bond
                                with thiol group of Cys residue at location 19"

( i x ) FEATURE:
                        ( A ) NAME/KEY: modified site
                        ( B ) LOCATION: 19
                        ( C ) IDENTIFICATION METHOD:
                        ( D ) OTHER INFORMATION: /note="thiol group of
                                Cys residue at location 19 connected by disulfide bond
                                with thiol group of Cys residue at location 2"

( x ) PUBLICATION INFORMATION:
                        ( A ) AUTHORS:
                        ( B ) TITLE:
                        ( C ) JOURNAL:
                        ( D ) VOLUME:
                        ( E ) ISSUE:
                        ( F ) PAGES:
                        ( G ) DATE:
                        ( H ) DOCUMENT NUMBER:
                        ( I ) FILING DATE:
                        ( J ) PUBLICATION DATE:
                        ( K ) RELEVANT RESIDUES IN SEQ ID NO:

( x i ) SEQUENCE DESCRIPTION: SEQ ID NO:3:

Lys  Cys  Phe  Gln  Trp  Gln  Arg  Asn  Met  Arg  Lys  Val  Arg  Gly  Pro
  1              5                        10                        15

Pro  Val  Ser  Cys  Ile
               20

( 2 ) INFORMATION FOR SEQ ID NO:4:

( i ) SEQUENCE CHARACTERISTICS:
                        ( A ) LENGTH: 20 amino acids
                        ( B ) TYPE: amino acid
                        ( C ) STRANDEDNESS: single
                        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                        ( A ) ORGANISM:
                        ( B ) STRAIN:
                        ( C ) INDIVIDUAL ISOLATE:
                        ( D ) DEVELOPMENTAL STAGE:
                        ( E ) HAPLOTYPE:
                        ( F ) TISSUE TYPE:
                        ( G ) CELL TYPE:
                        ( H ) CELL LINE:
                        ( I ) ORGANELLE:

( v i i ) IMMEDIATE SOURCE:
                        ( A ) LIBRARY:
                        ( B ) CLONE:

( v i i i ) POSITION IN GENOME:
                        ( A ) CHROMOSOME/SEGMENT:
                        ( B ) MAP POSITION:
                        ( C ) UNITS:

( i x ) FEATURE:
                        ( A ) NAME/KEY: modified site
                        ( B ) LOCATION: 2

(C) IDENTIFICATION METHOD:
                (D) OTHER INFORMATION: /note="Cys residue
                    having thiol group chemically modified to prevent
                    disulfide bond formation"

(ix) FEATURE:
                (A) NAME/KEY: modified site
                (B) LOCATION: 19
                (C) IDENTIFICATION METHOD:
                (D) OTHER INFORMATION: /note="Cys residue
                    having thiol group chemically modified to prevent
                    disulfide bond formation"

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(xi) SEQUENCE DESCRIPTION: SEQ ID NO:4:

Lys Xaa Phe Gln Trp Gln Arg Asn Met Arg Lys Val Arg Gly Pro
1               5                   10                  15

Pro Val Ser Xaa Ile
                20

(2) INFORMATION FOR SEQ ID NO:5:

(i) SEQUENCE CHARACTERISTICS:
                (A) LENGTH: 25 amino acids
                (B) TYPE: amino acid
                (C) STRANDEDNESS: single
                (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY: modified site
                (B) LOCATION: 3
                (C) IDENTIFICATION METHOD:
                (D) OTHER INFORMATION: /note="thiol group of
                    Cys residue at location 3 connected by disulfide bond
                    with thiol group of Cys residue at location 20"

(ix) FEATURE:
                (A) NAME/KEY: modified site
                (B) LOCATION: 20

(C) IDENTIFICATION METHOD:
(D) OTHER INFORMATION: /note="thiol group of
    Cys residue at location 20 connected by disulfide bond
    with thiol group of Cys residue at location 3"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:5:

Phe Lys Cys Arg Arg Trp Gln Trp Arg Met Lys Lys Leu Gly Ala
1               5                   10                  15

Pro Ser Ile Thr Cys Val Arg Arg Ala Phe
            20                  25

(2) INFORMATION FOR SEQ ID NO:6:

(i) SEQUENCE CHARACTERISTICS:
        (A) LENGTH: 38 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified site
        (B) LOCATION: 16
        (C) IDENTIFICATION METHOD:
        (D) OTHER INFORMATION: /note="thiol group of
            Cys residue at location 16 connected by disulfide bond
            with thiol group of Cys residue at location 33"

(ix) FEATURE:
        (A) NAME/KEY: modified site
        (B) LOCATION: 33
        (C) IDENTIFICATION METHOD:
        (D) OTHER INFORMATION: /note="thiol group of
            Cys residue at location 33 connected by disulfide bond
            with thiol group of Cys residue at location 16"

(x) PUBLICATION INFORMATION:
        (A) AUTHORS:
        (B) TITLE:

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:6:

```
Lys Asn Val Arg Trp Cys Thr Ile Ser Gln Pro Glu Trp Phe Lys
 1               5                  10                  15
Cys Arg Arg Trp Gln Trp Arg Met Lys Lys Leu Gly Ala Pro Ser
                20                  25                  30
Ile Thr Cys Val Arg Arg Ala Phe
                35
```

(2) INFORMATION FOR SEQ ID NO:7:

(i) SEQUENCE CHARACTERISTICS:
        (A) LENGTH: 32 amino acids
        (B) TYPE: amino acid
        (C) STRANDEDNESS: single
        (D) TOPOLOGY: linear     (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified site
        (B) LOCATION: 10
        (C) IDENTIFICATION METHOD:
        (D) OTHER INFORMATION: /note="thiol group of
            Cys residue at location 10 connected by disulfide bond
            with thiol group of Cys residue at location 27"

(ix) FEATURE:
        (A) NAME/KEY: modified site
        (B) LOCATION: 27
        (C) IDENTIFICATION METHOD:
        (D) OTHER INFORMATION: /note="thiol group of
            Cys residue at location 27 connected by disulfide bond
            with thiol group of Cys residue at location 10"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:

(H) DOCUMENT NUMBER:
(I) FILING DATE:
(J) PUBLICATION DATE:
(K) RELEVANT RESIDUES IN SEQ ID NO:

(xi) SEQUENCE DESCRIPTION: SEQ ID NO:7:

```
Thr Ile Ser Gln Pro Glu Trp Phe Lys Cys Arg Arg Trp Gln Trp
 1               5                  10                   15
Arg Met Lys Lys Leu Gly Ala Pro Ser Ile Thr Cys Val Arg Arg
                20                  25                   30
Ala Phe
```

(2) INFORMATION FOR SEQ ID NO:8:

(i) SEQUENCE CHARACTERISTICS:
        (A) LENGTH: 36 amino acids
        (B) TYPE: amino acid
        (C) STRANDEDNESS: single
        (D) TOPOLOGY: linear     (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified site
        (B) LOCATION: 9
        (C) IDENTIFICATION METHOD:
        (D) OTHER INFORMATION: /note="thiol group of
            Cys residue at location 9 connected by disulfide bond
            with thiol group of Cys residue at location 26"

(ix) FEATURE:
        (A) NAME/KEY: modified site
        (B) LOCATION: 26
        (C) IDENTIFICATION METHOD:
        (D) OTHER INFORMATION: /note="thiol group of
            Cys residue at location 26 connected by disulfide bond
            with thiol group of Cys residue at location 9"

(ix) FEATURE:
        (A) NAME/KEY: modified site
        (B) LOCATION: 35
        (C) IDENTIFICATION METHOD:
        (D) OTHER INFORMATION: /note="thiol group of
            Cys residue at location 35 connected by disulfide bond
            with thiol group of Cys residue at location 10 of
            SEQ ID NO. 9"

(x) PUBLICATION INFORMATION:
        (A) AUTHORS:
        (B) TITLE:
        (C) JOURNAL:
        (D) VOLUME:

-continued ( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:8:

```
Val Ser Gln Pro Glu Ala Thr Lys Cys Phe Gln Trp Gln Arg Asn
1               5                   10                  15

Met Arg Lys Val Arg Gly Pro Pro Val Ser Cys Ile Lys Arg Asp
                20                  25                  30

Ser Pro Ile Gln Cys Ile
                35
```

( 2 ) INFORMATION FOR SEQ ID NO:9:

( i ) SEQUENCE CHARACTERISTICS:
( A ) LENGTH: 11 amino acids
( B ) TYPE: amino acid
( C ) STRANDEDNESS: single
( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:
( A ) LIBRARY:
( B ) CLONE:

( v i i i ) POSITION IN GENOME:
( A ) CHROMOSOME/SEGMENT:
( B ) MAP POSITION:
( C ) UNITS:

( i x ) FEATURE:
( A ) NAME/KEY: modified site
( B ) LOCATION: 10
( C ) IDENTIFICATION METHOD:
( D ) OTHER INFORMATION: /note="thiol group of
Cys residue at location 10 connected by disulfide bond
with thiol group of Cys residue at location 35 of
SEQ ID NO. 8"

( x ) PUBLICATION INFORMATION:
( A ) AUTHORS:
( B ) TITLE:
( C ) JOURNAL:
( D ) VOLUME:
( E ) ISSUE:
( F ) PAGES:
( G ) DATE:
( H ) DOCUMENT NUMBER:
( I ) FILING DATE:
( J ) PUBLICATION DATE:
( K ) RELEVANT RESIDUES IN SEQ ID NO:

( x i ) SEQUENCE DESCRIPTION: SEQ ID NO:9:

```
Gly Arg Arg Arg Arg Ser Val Gln Trp Cys Ala
1               5                   10
```

( 2 ) INFORMATION FOR SEQ ID NO:10:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear     ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: modified site
        ( B ) LOCATION: 4
        ( C ) IDENTIFICATION METHOD:
        ( D ) OTHER INFORMATION: /note="thiol group of
            Cys residue at location 4 connected by disulfide bond
            with thiol group of Cys residue at location 21"

( i x ) FEATURE:
        ( A ) NAME/KEY: modified site
        ( B ) LOCATION: 21
        ( C ) IDENTIFICATION METHOD:
        ( D ) OTHER INFORMATION: /note="thiol group of
            Cys residue at location 21 connected by disulfide bond
            with thiol group of Cys residue at location 4"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:10:

Ala Thr Lys Cys Phe Gln Trp Gln Arg Asn Met Arg Lys Val Arg
1               5                   10                  15

Gly Pro Pro Val Ser Cys Ile Lys Arg Asp
                20              25

EXAMPLES

The following Examples illustrate the present invention more specifically. These Examples are not intended to limit the invention in any manner.

EXAMPLE 1

Preparation of a peptide mixture containing lactoferricin is exemplified as follows.

Bovine lactoferrin (2.0 kg; Morinaga Milk Industry Co., Ltd; purity, approximately 90%) isolated from skim milk was dissolved in distilled water at a concentration of 5% (w/v) and the pH was adjusted to 3.0 by addition of 1N HCl. Crystalline pepsin (Difco Laboratories) was added to a final concentration of 3% (w/w of substrate) and hydrolysis was performed at 37° C. for 4 h. The reaction was terminated by heating at 80° C. for 15 min. The pH of the resulting peptide mixture was adjusted to 7.0 by addition of 1N NaOH and insoluble peptides were removed by filtration. The peptide solution was spray-dried to obtain 1.9 kg of powdered material.

EXAMPLE 2

Production of lactoferricin in high purity using a carboxymethyl moiety-containing cation-exchange chromatography medium is exemplified as follows.

For use as the starting material, 50 g of the peptide mixture obtained in Example 1 was dissolved in distilled water at a final concentration of 5% (w/v). CARBOXYMETHYL-TOYOPEAL 650S (Tosoh Corp.) was rinsed and equilibrated with 100 mM $KH_2PO_4$-$K_2HPO_4$ buffer, pH 7.8 before use and approximately 400 ml of this cation-exchange medium was used. The starting material was initially contacted with the cation-exchange medium in a stirred tank, then the liquid was collected and the medium was transferred to a chromatographic column (10 cm×8 cm i.d.). The collected liquid was again contacted with the medium in the column, then the cation-exchange medium was rinsed with the buffer, at a flow rate of about 20 ml/min, to remove the unbound peptides. Rinsing of the medium was continued until the protein content of the buffer eluted from the medium declined to a low level, as indicated by an absorbance at 280 nm of about 0.06. The lactoferricin was desorbed from the medium at constant pH with 2M ammonium acetate, pH 7.8. Desalting of the lactoferricin solution thus obtained was accomplished using 0.5 liters of BUTYL-TOYOPEARL 650M (Tosoh Corp.). The lactoferricin solution was contacted with the hydrophobic medium in a chromatographic column (10×8 cm i.d.) and the medium was rinsed with about 5 liters of water to remove the buffer salts. Finally, lactoferricin was desorbed with 10 mM HCl and freeze-dried to obtain 1.4 grams of powdered product. The purity of the lactoferricin obtained was 92% as estimated by reverse-phase high performance liquid chromatography.

EXAMPLE 3

Production of lactoferricin in high purity using a butyl moiety-containing hydrophobic interaction chromatography medium is exemplified as follows.

For use as the starting material, 256 g of the peptide mixture obtained in Example 1 was dissolved in distilled water at a final concentration of 5% (w/v). BUTYL-TOYOPEARL 650M (Tosoh Corp.) was rinsed and equilibrated with water before use and approximately 1100 ml of this hydrophobic medium was used. The starting material was initially contacted with the hydrophobic medium in a stirred tank, then the liquid was collected and the medium was transferred to a chromatographic column (22 cm×8 cm i.d.). The collected liquid was again contacted with the medium in the column, then the hydrophobic medium was rinsed with water, at a flow rate of about 100 ml/min, to remove the unbound peptides. Rinsing of the medium was continued until the protein content of the water eluted from the medium declined to a low level, as indicated by an absorbance at 280 nm of about 0.06. The bound peptides including lactoferricin were desorbed from the medium with 10 mM HCl and mixed with an equal volume of McIlvaine buffer, pH 7.0 (prepared by combining solutions of 0.1M citric acid and 0.2M $Na_2HPO_4$ in a ratio of 177:824). The resulting buffered peptide solution was contacted with the hydrophobic medium and the medium was rinsed with about 2 liters of the same buffer. Lactoferricin was desorbed selectively from the medium at a constant pH with about 3 liters of McIlvaine buffer, pH 5.0 (prepared by combining solutions of 0.1M citric acid and 0.2M $Na_2HPO_4$ in a ratio of 485:515). The hydrophobic medium was reconditioned by rinsing with 10 mM HCl and then with water. Desalting of the lactoferricin solution thus obtained was accomplished using the reconditioned BUTYL-TOYOPEARL 650M. The lactoferricin solution was adjusted to pH 7.0, by addition of 1N NaOH, and contacted with the hydrophobic medium, then the medium was rinsed with about 10 liters of water to remove the buffer salts. Finally, lactoferricin was desorbed with 10 mM HCl and freeze-dried to obtain 3.5 grams of powdered product. The purity of the lactoferricin obtained was 98% as estimated by reverse-phase high performance liquid chromatography.

EXAMPLE 4

Production of lactoferricin in high purity using a butyl moiety-containing hydrophobic interaction chromatography medium is further exemplified as follows.

For use as the starting material, 233 g of the peptide mixture obtained in Example 1 was dissolved in distilled water at a final concentration of 5% (w/v). The starting material was processed as described in Example 3, using 1100 ml of BUTYL-TOYOPEARL 650M (Tosoh Corp.), except desalting was accomplished by ultrafiltration dialysis using a Romicon Model 1.0-43- PM1 hollow filter cartridge having a molecular weight cut-off of 1000. The lactoferricin solution obtained was freeze-dried to obtain 1.6 grams of powdered product. The purity of the lactoferricin obtained was 98% as estimated by reverse-phase high performance liquid chromatography.

EXAMPLE 5

Production of lactoferricin in high purity using a butyl moiety-containing hydrophobic interaction chromatography medium is further exemplified as follows.

For use as the starting material, 600 g of the peptide mixture obtained in Example 1 was dissolved in distilled water at a final concentration of 5% (w/v). BUTYL-TOYOPEARL 650M (Tosoh Corp.) was rinsed and equilibrated with water before use and approximately 3000 ml of this hydrophobic gel was used. The starting material was initially contacted with the hydrophobic medium in a stirred tank, then the liquid was collected and the medium was transferred to a chromatographic column (10 cm×20 cm i.d.). The collected liquid was again contacted with the medium in the column, then the hydrophobic medium was rinsed with water, at a flow rate of about 100 ml/min, to remove the unbound peptides. Rinsing of the medium was continued until the protein content of the water eluted from the medium declined to a low level, as indicated by an absorbance at 280 nm of about 0.06. The bound peptides including lactoferricin were desorbed from the medium with 10 mM HCl and mixed with an equal volume of McIlvaine buffer, pH 7.0 (prepared by combining solutions of 0.1M citric acid and 0.2M $Na_2HPO_4$ in a ratio of 177:824). The resulting buffered peptide solution was contacted with the hydrophobic medium and the medium was rinsed with about 6 liters of the same buffer. Lactoferricin was desorbed selectively from the medium at a constant pH with about 9 liters of McIlvaine buffer, pH 5.0 (prepared by combining solutions of 0.1M citric acid and 0.2M $Na_2HPO_4$ in a ratio of 485:515). Desalting of the lactoferricin solution thus obtained was accomplished using same 3000 ml of BUTYL-TOYOPEARL 650M. The lactoferricin solution was adjusted to pH 7.0, by addition of 1N NaOH, and contacted with the hydrophobic medium, then the medium was rinsed with about 30 liters of water to remove the buffer salts. Finally, lactoferricin was desorbed with 10 mM HCl and freeze-dried to obtain 10.5 grams of powdered product. The purity of the product was 99% as estimated by reverse-phase high performance liquid chromatography.

What is claimed is:

1. A process for large-scale production of an antimicrobial peptide having the sequence Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe in high purity which comprises the steps of:
   a) contacting a mixture of peptides containing the antimicrobial peptide which is prepared by enzymatically hydrolysing bovine lactoferrin or bovine milk protein containing lactoferrin with a carboxyl moiety-containing cation-exchange chromatographic medium to adsorb the antimicrobial peptide,
   b) rinsing the chromatographic medium with a buffer to elute peptides other than the antimicrobial peptide,
   c) desorbing the antimicrobial peptide in solution from the rinsed cation-exchange chromatographic medium with a solution containing a salt at a concentration of 1 to 4 moles per liter at pH 7–8, and
   d) desalting the desorbed antimicrobial peptide solution, whereby the antimicrobial peptide of at least 90% by weight purity is obtained.

2. The process according to claim 1, wherein the chromatographic medium is subjected to rinsing with a buffer selected from the group consisting of $NaH_2PO_4$-$Na_2HOP_4$, $KH_2PO_4$-$K_2HPO_4$, $NaH_2PO_4$-$K_2HPO_4$, $KH_2PO_4$-$Na_2HPO_4$, citric acid-$Na_2HPO_4$, acetic acid-sodium acetate and Glycine-NaOH at a pH of 7.8.

3. The process according to claim 2, wherein the chromatographic medium is subjected to desorbing the antimicrobial peptide with a solution containing a salt selected from the group consisting of ammonium chloride, ammonium acetate, sodium chloride, and potassium chloride.

4. A process for large-scale production of an antimicrobial peptide having the sequence Phe-Lys-Cys-Arg-Arg-Trp-Gln-Trp-Arg-Met-Lys-Lys-Leu-Gly-Ala-Pro-Ser-Ile-Thr-Cys-Val-Arg-Arg-Ala-Phe in high purity which comprises the steps of:
   a) contacting a mixture of peptides containing the antimicrobial peptide, which is prepared by enzymatically hydrolysing bovine lactoferrin or bovine milk protein containing lactoferrin with a hydrophobic chromatographic medium, to adsorb the antimicrobial peptide,
   b) rinsing the chromatographic medium with a buffer at a pH of 6.5–7.5 to elute peptides other than the antimicrobial peptide,
   c) desorbing the antimicrobial peptide in solution from the rinsed hydrophobic chromatographic medium with a dilute solution of acid or a buffer at pH 4.5–5.5, and
   d) desalting the desorbed antimicrobial peptide solution, whereby the antimicrobial peptide having the purity of at least 90% by weight is obtained.

5. The process according to claim 4, wherein the hydrophobic chromatographic medium contains a moiety selected from the group consisting of a butyl moiety, a hexyl moiety, an octyl moiety, a phenyl moiety, and an octylamine moiety.

6. The process according to claim 4, wherein the hydrophobic chromatographic medium is subjected to rinsing with a buffer selected from the group consisting of $NaH_2PO_4$-$Na_2HPO_4$, $KH_2PO_4$-$K_2HPO_4$, $NaH_2PO_4$-$K_2HPO_4$, $KH_2PO_4$-$Na_2HPO_4$, citric acid-$Na_2HPO_4$, and acetic acid-sodium acetate at pH of 6.5–7.5.

7. The process according to claim 4, wherein the antimicrobial peptide is desorbed with a buffer selected from the group consisting of $NaH_2PO_4$-$Na_2HPO_4$, $KH_2PO_4$-$K_2HPO_4$, $NaH_2PO_4$-$K_2HPO_4$, $KH_2PO_4$-$Na_2HPO_4$, citric acid-$Na_2HPO_4$, and acetic acid-sodium acetate at a pH of 4.5–5.5.

8. The process according to claim 4, wherein the antimicrobial peptide is desorbed with a dilute solution of acid selected from the group consisting of hydrochloric acid, sulfuric acid, phosphoric acid, acetic acid, and citric acid at a pH of 4.5–5.5.

9. The process according to claim 1, wherein the desalting is performed by electrodialysis or ultrafiltration using a semipermeable membrane or hollow fiber cartridge having a molecular weight cut-off of 3000 or less.

10. The process according to claim 10, wherein the desalting is performed by contacting the desorbed antimicrobial peptide with a hydrophobic chromatographic medium, rinsing the medium with water, and desorbing the antimicrobial peptide from the medium with an aqueous solution of acid.

11. The process according to claim 4, wherein the desalting is performed by electrodialysis or ultrafiltration using a semipermeable membrane or hollow fiber cartridge having a molecular weight cut-off or 3000 or less.

12. The process according to claim 4, wherein the desalting is performed by contacting the desorbed antimicrobial peptide with a hydrophobic chromatographic medium, rinsing the medium with water, and desorbing the antimicrobial peptide from the medium with an aqueous solution of acid.

* * * * *